(12) United States Patent
Ribnick et al.

(10) Patent No.: US 9,031,312 B2
(45) Date of Patent: May 12, 2015

(54) RAPID PROCESSING AND DETECTION OF NON-UNIFORMITIES IN WEB-BASED MATERIALS

(75) Inventors: Evan J. Ribnick, St. Louis Park, MN (US); Kenneth G. Brittain, Cottage Grove, MN (US); John A. Ramthun, Hudson, WI (US); Derek H. Justice, Cary, NC (US); Guillermo Sapiro, Durham, NC (US)

(73) Assignee: 3M Innovative Properties Company, St. Paul, MN (US)

( * ) Notice: Subject to any disclaimer, the term of this patent is extended or adjusted under 35 U.S.C. 154(b) by 75 days.

(21) Appl. No.: 13/882,781

(22) PCT Filed: Oct. 28, 2011

(86) PCT No.: PCT/US2011/058250
§ 371 (c)(1), (2), (4) Date: May 1, 2013

(87) PCT Pub. No.: WO2012/064522
PCT Pub. Date: May 18, 2012

(65) Prior Publication Data
US 2013/0236082 A1    Sep. 12, 2013

Related U.S. Application Data

(60) Provisional application No. 61/413,250, filed on Nov. 12, 2010.

(51) Int. Cl.
*G06T 7/00* (2006.01)
*G01N 21/89* (2006.01)

(52) U.S. Cl.
CPC .............. *G06T 7/001* (2013.01); *G01N 21/89* (2013.01); *G06T 7/0004* (2013.01);

(Continued)

(58) Field of Classification Search
None
See application file for complete search history.

(56) References Cited

U.S. PATENT DOCUMENTS 4,728,800 A * 3/1988 Surka .................. 250/559.42
5,308,010 A * 5/1994 Hakiel ...................... 242/534

(Continued)

FOREIGN PATENT DOCUMENTS

JP    2003-317082    11/2003
JP    2004-47939    2/2004

(Continued)

OTHER PUBLICATIONS

Andoni et al., "Near-Optimal Hashing Algorithms for Approximate Nearest Neighbor in High Dimensions", *Communications of the ACM*, vol. 51, No. 1, Jan. 2008, pp. 117-122.

(Continued)

*Primary Examiner* — Nancy Bitar
(74) *Attorney, Agent, or Firm* — James A. Baker (57) ABSTRACT

A computerized inspection system is described for detecting the presence of non-uniformity defects and providing output indicative of a severity of each type of non-uniformity defect. Techniques are described that increase the throughput of the inspection system. Algorithmic and hardware approaches are described to significantly decrease the average amount of time required to inspect a given quantity of material that is expected to be mostly uniform. The techniques described herein involve dynamic selection of which image features to compute by starting with a base feature set and only triggering additional feature computations as needed until the features are sufficient to compute a severity for each type of non-uniformity defect. The number of features extracted and the order in which the features are extracted is dynamically determined in real-time to reduce a cost associated with the feature extraction.

12 Claims, 8 Drawing Sheets

(52) U.S. Cl.
CPC ........... *G06T 2207/10024* (2013.01); *G06T 2207/20016* (2013.01); *G06T 2207/20076* (2013.01); *G06T 2207/20081* (2013.01); *G06T 2207/30124* (2013.01)

(56) References Cited

U.S. PATENT DOCUMENTS

| | | | |
|---|---|---|---|
| 5,893,055 A * | 4/1999 | Chen | 702/189 |
| 5,911,139 A | 6/1999 | Jain et al. | |
| 5,999,636 A * | 12/1999 | Juang | 382/112 |
| 6,411,860 B1 * | 6/2002 | Chen | 700/129 |
| 6,445,834 B1 | 9/2002 | Rising, III | |
| 6,539,106 B1 | 3/2003 | Gallarda et al. | |
| 6,778,694 B1 * | 8/2004 | Alexandre | 382/141 |
| 6,847,733 B2 | 1/2005 | Savakis et al. | |
| 6,870,965 B2 | 3/2005 | Kim et al. | |
| 6,999,614 B1 | 2/2006 | Bakker et al. | |
| 7,023,446 B1 | 4/2006 | Iwasaki | |
| 7,113,994 B1 | 9/2006 | Swift et al. | |
| 7,283,659 B1 | 10/2007 | Bakker et al. | |
| 7,359,544 B2 * | 4/2008 | Gao et al. | 382/145 |
| 7,529,732 B2 | 5/2009 | Liu et al. | |
| 7,545,985 B2 * | 6/2009 | Zhang et al. | 382/224 |
| 2002/0009220 A1 | 1/2002 | Tanaka | |
| 2002/0015526 A1 * | 2/2002 | Nomura et al. | 382/199 |
| 2002/0110269 A1 * | 8/2002 | Floeder et al. | 382/141 |
| 2003/0202703 A1 | 10/2003 | Ogi | |
| 2004/0120569 A1 | 6/2004 | Hung et al. | |
| 2004/0218806 A1 | 11/2004 | Miyamoto et al. | |
| 2005/0135667 A1 | 6/2005 | Saarela et al. | |
| 2006/0045356 A1 | 3/2006 | Turtinen et al. | |
| 2010/0188735 A1 * | 7/2010 | Tamaoki | 359/341.3 |
| 2011/0188735 A1 * | 8/2011 | Hosoya et al. | 382/149 |

FOREIGN PATENT DOCUMENTS

| | | |
|---|---|---|
| JP | 2008-175588 | 7/2008 |
| JP | 2010-54346 | 3/2010 |
| KR | 10-2001-0101697 | 10/2002 |
| WO | WO 02/077870 | 10/2002 |
| WO | WO 2010/059679 | 5/2010 |

OTHER PUBLICATIONS

Day et al., "Efficient Algorithms for Agglomerative Hierarchical Clustering Methods", *Journal of Classification*, vol. 1, No. 1, (1984), pp. 7-24.

Lafon et al., "Diffusion Maps and Coarse-Graining: A Unified Framework for Dimensionality Reduction, Graph Partitioning, and Data Set Parameterization", *IEEE Transactions on Pattern Analysis and Machine Intelligence*, vol. 28, No. 9, (2006), pp. 1393-1403.

Moore, "The Anchors Hierarchy: Using the Triangle Inequality to Survive High Dimensional Data", Uncertainty in Artificial Intelligence Proceedings, (2000), pp. 397-405.

Seung et al., "Cognition: The Manifold Ways of Perception", *Science*, vol. 290, Dec. 22, 2000, pp. 2268-2269.

Tuzel et al., "Region Covariance: A Fast Descriptor for Detection and Classification", Proceedings of the European Conference on Computer Vision, (2006), pp. 589-600.

Zhu et al., "Learning from Labeled and Unlabeled Data with Label Propagation", CMU CALD Technical Report CMU-CALD-02-107, (2002), 19 pages.

* cited by examiner

RAPID PROCESSING AND DETECTION OF NON-UNIFORMITIES IN WEB-BASED MATERIALS

CROSS REFERENCE TO RELATED APPLICATION

This application claims the benefit of U.S. Provisional Patent Application No. 61/413,250, filed Nov. 12, 2010, the disclosure of which is incorporated by reference herein in its entirety.

TECHNICAL FIELD

The invention relates to automated inspection systems, such as computerized systems for inspection of moving webs.

BACKGROUND

Computerized inspection systems for the analysis of moving web materials have proven critical to modern manufacturing operations. The goal of a production line is to produce material which is perfectly uniform and devoid of variability. However, non-uniformity is a common problem when manufacturing web-based materials. This can be caused by any number of process variables or formulation errors. Consequently, it is becoming increasingly common to deploy imaging-based inspection systems that can automatically classify the quality of a manufactured product based on digital images captured by optical inspection sensors (e.g., cameras). Some inspection systems apply algorithms, which are often referred to as "classifiers," that attempt to assign a rating to each captured digital image (i.e., "sample") indicating whether the sample, or portions thereof, is acceptable or unacceptable, in the simplest case.

These inspection systems often attempt to identify "point" defects in which each defect is localized to a single area of the manufactured material. However, other types of defects, referred to "non-uniformity" defects or "non-uniformities" may exist in which the web material exhibits non-uniform variability over a large area. Examples of such non-uniformities include mottle, chatter, banding, and streaks. Non-uniformity-type defects such as these are by definition distributed and non-localized. As a result, such defects may be more difficult for computerized inspection systems to detect and quantify than localized, point defects.

When attempting to detect non-uniformities in manufactured material, the inspection system typically collects and processes sample images to extract features indicative of particular non-uniformities. On the basis of these features, the inspection system applies one or more classifiers to produce an assessment of the severity of the non-uniformity. The feature extraction can be computational intensive and a limiting factor of the inspection process. For example, in this step, high resolution images containing several million pixels are reduced to perhaps no more than fifty representative numbers (or features) through routines that may involve filtering, morphological, temporal, spectral, or statistical processing. The resulting numbers then form the basis for assessing the quality of the underlying product. The amount of time required to collapse millions of pixel values into tens of informative numbers can be substantial and, as such, cannot be performed in real-time for fast production rates, even on modern computers. One possibility could be to purchase higher quantities of more expensive computers, but this solution may make the cost of the inspection systems prohibitively expensive and gives rise to additional implementation problems of data distribution and result aggregation.

SUMMARY

In general, this disclosure describes a computerized inspection system for detecting the presence of non-uniformity defects and providing output indicative of a severity of each defect. Techniques are described that increase the throughput of the inspection system that is designed to detect and classify specific patterns in a web-manufactured material. Algorithmic and hardware approaches are described to significantly decrease the average amount of time required to inspect a given quantity of material that is expected to be mostly uniform. As such, the techniques may lead to substantial productivity gains. The algorithmic techniques described herein involve dynamic (i.e., online) determination of which image features to compute by starting with a base feature set and only triggering additional feature computations as needed.

In one embodiment, an online computerized inspection system is described for inspecting web material in real-time and computing a severity of a non-uniformity defect as the web material is manufactured. The inspection system comprises a memory to store a model that defines a chain of dynamic triggers for selecting in real-time which features to extract from a sample image of the web material. A computer executes software to process a sample image captured from a manufactured web material currently being manufactured to extract a first set of features. The software applies the model to dynamically trigger selection of additional sets of features to extract from the sample image until the extracted features are sufficient to compute a severity level of a non-uniformity defect for the web material.

In another embodiment, a method is described for inspecting web material in real-time and computing a severity of a non-uniformity defect as the web material is manufactured. The method comprises receiving, with an online computerized inspection system, an image captured from a web material being manufactured, processing the image with the inspection system with the inspection system to extract a first set of features, and processing the first set of features with the inspection system to determine whether a severity level of a non-uniform defect for the web material can be computed. The method further comprises upon determining that the severity level cannot be computed from the first set of features, applying a model to dynamically select a second set of features to extract from the image, processing the image with the inspection system to extract the second set of features, and processing the second set of features with the inspection system to determine whether the severity level of the non-uniform defect for the web material can be computed. The method further comprises, upon determining that the severity level can be computed from the first set of features and the second set of features, computing the severity level for the non-uniformity defect for the web material with the inspection system.

The techniques described herein have applicability and usefulness in numerous product lines, including any material that is produced on a web. The techniques have broad applicability to a wide range of products in which uniformity is important. A few examples are optical films, window films, and abrasives.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
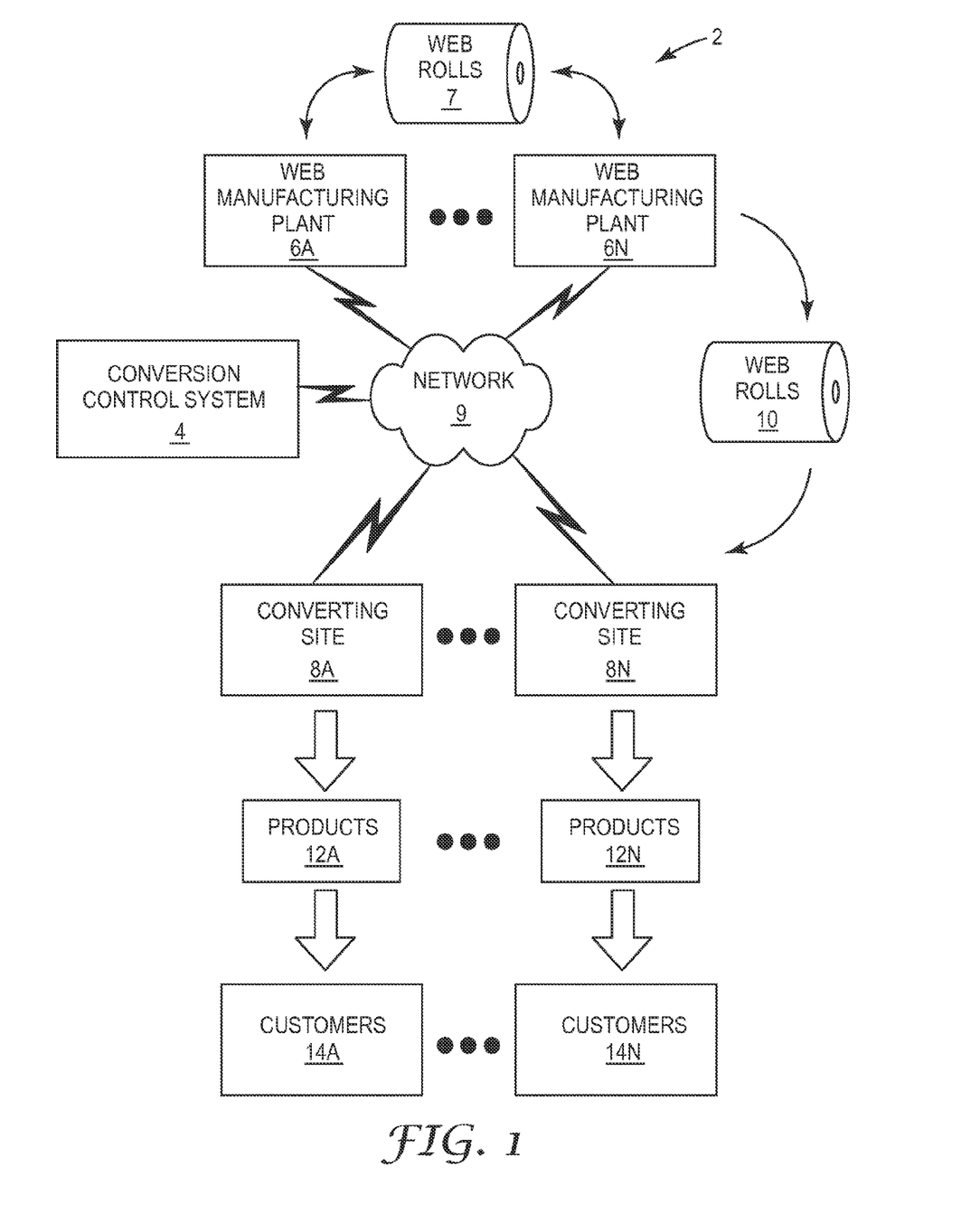
FIG. 1 is a block diagram illustrating an example web manufacturing and conversion system in which the techniques described herein may be applied.

FIG. 1 is a block diagram illustrating an example system 2 in which the techniques described herein may be applied. Web manufacturing plants 6A-6N (web manufacturing plants 6) represent manufacturing sites that produce and ship web material in the form of web rolls 7. Web manufacturing plants 6 may be geographically distributed, and each of the web manufacturing plants may include one or more manufacturing process lines. In general, web rolls 7 may be manufactured by any of manufacturing plants 6 and shipped between the web manufacturing plants for additional processing. Finished web rolls 10 are shipped to converting sites 8A-8N (converting sites 8) for conversion into products 12A-12N (products 12). As shown in FIG. 1, conversion control system 4, web manufacturing plants 6A-6M (web manufacturing plants 6) and converting sites 8A-8N (converting sites 8) are interconnected by a computer network 9 for exchanging information (e.g., defect information) related to manufacture of the web material and conversion into products 12.

In general, web rolls 7, 10 may contain manufactured web material that may be any sheet-like material having a fixed dimension in one direction and either a predetermined or indeterminate length in the orthogonal direction. Examples of web materials include, but are not limited to, metals, paper, wovens, non-wovens, glass, polymeric films, flexible circuits or combinations thereof. Metals may include such materials as steel or aluminum. Wovens generally include various fabrics. Non-wovens include materials, such as paper, filter media, or insulating material. Films include, for example, clear and opaque polymeric films including laminates and coated films.

Converting sites 8 may receive finished web rolls 10 from web manufacturing plants 6 and convert finished web rolls 10 into individual sheets for incorporation into products 12 for sale to customers 14A-14N (customers 14). Converting systems may determine into which products 14 a given finished web roll 10 is converted based on a variety of criteria, such as grade levels associated with the product. That is, the selection process of which sheets should be incorporated into which products 12 may be based on the specific grade levels each sheet satisfies. In accordance with the techniques described herein, converting sites 8 may also receive data regarding anomalies, i.e. potential defects, in the finished web rolls 10. Ultimately, converting sites 8 may convert finished web rolls 10 into individual sheets which may be incorporated into products 12 for sale to customers 14A-14N (customers 14).

In order to produce a finished web roll 10 that is ready for conversion into individual sheets for incorporation into products 12, unfinished web rolls 7 may need to undergo processing from multiple process lines either within one web manufacturing plant, for instance, web manufacturing plant 6A, or within multiple manufacturing plants. For each process, a web roll is typically used as a source roll from which the web is fed into the manufacturing process. After each process, the web is typically collected again into a web roll 7 and moved to a different product line or shipped to a different manufacturing plant, where it is then unrolled, processed, and again collected into a roll. This process is repeated until ultimately a finished web roll 10 is produced. For many applications, the web materials for each of web rolls 7 may have numerous coatings applied at one or more production lines of one or more web manufacturing plants 6. The coating is generally applied to an exposed surface of either a base web material, in the case of the first manufacturing process, or a previously applied coating in the case of a subsequent manufacturing process. Examples of coatings include adhesives, hardcoats, low adhesion backside coatings, metalized coatings, neutral density coatings, electrically conductive or nonconductive coatings, or combinations thereof.

Figure 2:
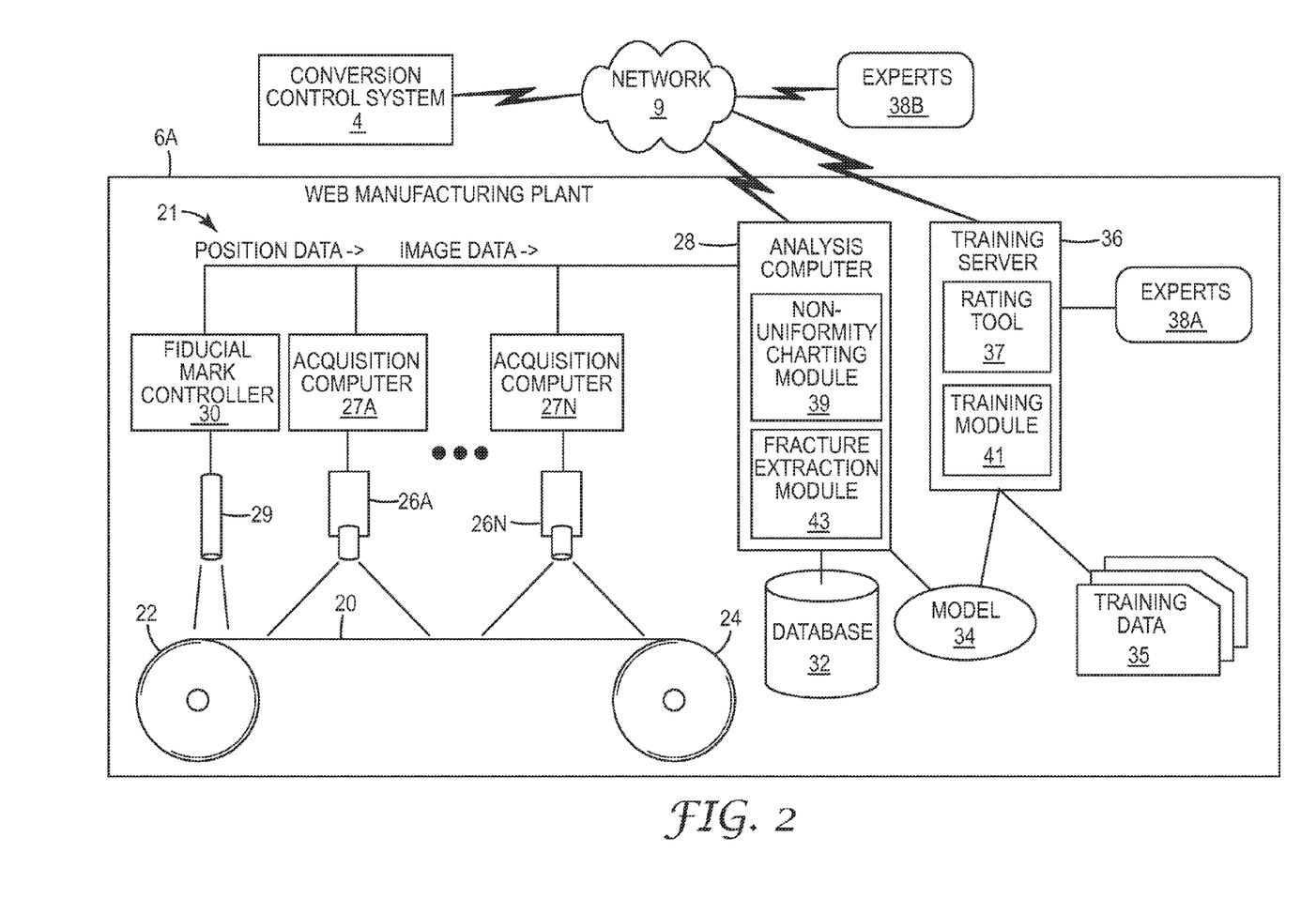
FIG. 2 is a block diagram illustrating an exemplary embodiment of an inspection system in an exemplary web manufacturing plant.

During each manufacturing process for a given one of web rolls 7, one or more inspection systems acquire anomaly information for the web. For example, as illustrated in FIG. 2, an inspection system for a production line may include one or more image acquisition devices positioned in close proximity to the continuously moving web as the web is processed, e.g., as one or more coatings are applied to the web. The image acquisition devices scan sequential portions of the continuously moving web to obtain digital images. The inspection systems analyze the images with one or more algorithms to produce so-called "local" anomaly information that may represent an actual "defect" depending upon the ultimate product 12 into which the web is converted. The inspection systems may, for example, produce anomaly information for "point" defects in which each defect is localized to a single area. As another example, the inspections systems may produce anomaly information for "non-uniform" defects or "non-uniformities" in which the web material exhibits non-uniform variability over a large area larger than that of point defects. Examples of such non-uniformities include mottle, chatter, banding, and streaks.

The inspection systems within web manufacturing plants 6 may apply algorithms for detecting the presence of non-uniformity defects and providing output indicative of a severity of each defect in real-time as the web is manufactured. For example, the computerized inspection systems may provide real-time feedback to users, such as process engineers, within web manufacturing plants 6 regarding the presence of non-uniformities and their severity, thereby allowing the users to quickly respond to an emerging non-uniformity by adjusting process conditions to remedy the problem without significantly delaying production or producing large amounts of unusable material. The computerized inspection system may apply algorithms to compute the severity level by ultimately assigning a rating label for the non-uniformity (e.g., "good" or "bad") or by producing a measurement of non-uniformity severity of a given sample on a continuous scale or more accurately sampled scale, such as 1.63 on a scale from 0 to 10.

During this process, the inspection systems may apply techniques described herein to dynamically (i.e., in real-time during manufacture of a web material) determine which image features to compute. In one example, the inspection systems start with extraction of a base feature set and only triggering the computations for additional feature as needed. For each sample image acquired, the techniques build a "best feature set" in real-time by using the results from successively larger feature sets to trigger additional feature computations. The inspection systems start with a baseline feature set, then based on the values of the base feature set decide which extra features (if any) to compute. Similarly, these additional feature sets are analyzed to determine which additional features are needed. The decision at each step of the feature extraction process is referred to herein as a potential trigger event. In one embodiment, the inspection systems makes the decision whether to trigger the computation of additional features at each potential trigger event as to optimize the expected gain in classification accuracy under a controlled Markov chain model.

In some embodiments, analysis computers of the inspection systems process the captured digital images by application of a continuous ranking model that has been developed based on training data. The training data is typically processed during a "training phase" of the algorithms and the continuous ranking model is developed to best match the training data. That is, after the training phase and development of the continuous ranking model, application of the continuous ranking model to the training data will label the training data with a high probability of correctness. Once the model has been developed from the training data, the analysis computers apply the model to samples captured from newly manufactured product, potentially in real-time, during the "classification phase" of the processing and provide a continuous charting of non-uniformity severity that is not constrained to discrete rating labels, such as "acceptable" of "unacceptable," or a "1," "3," or "5," the computerized inspection system may provide a continuous ranking of samples. For example, the computerized inspection system may apply algorithms to produce measurements of severity for non-uniformity defects within a web material on a continuous scale, such as 1.63 on a scale from 0 to 10. Moreover, the continuous ranking model used to achieve the continuous ranking of samples may be developed from a set of training images for which non-uniformity severity levels are known only on a coarsely discretized scale.

In some embodiments, additional analysis of digital images for a given manufactured web may be performed offline by conversion control system 4. Based on the classifications for a given web, conversion control system 4 may select and generate a conversion plan for each web roll 10. The analysis of the digital images and determination of the severity level may be application-specific in that a certain non-uniformity may result in a defect in one product, e.g., product 12A, whereas the anomaly may not cause a defect in a different product, e.g., product 12B. Each conversion plan represents defined instructions for processing a corresponding finished web roll 10 for creating products 12, which may ultimately be sold to customers 14. For example, a web roll 10 may be converted into final products, e.g., sheets of a certain size, for application to displays of notebook computers. As another example, the same web roll 10 may instead be converted into final products for application to displays of cell phones. Conversion control system 4 may identify which product best achieves certain parameters, such as a maximum utilization of the web, in view of the different defect detection algorithms that may be applied to the anomalies.

FIG. 2 is a block diagram illustrating an exemplary embodiment of an inspection system located within a portion of a web process line 21 in exemplary web manufacturing plant 6A of FIG. 1. In the exemplary embodiment, a segment of a web 20 is positioned between two support rolls 22, 24. Image acquisition devices 26A-26N (image acquisition devices 26) are positioned in close proximity to the continuously moving web 20 and scan sequential portions of the continuously moving web 20 to obtain image data. Acquisition computers 27 collect image data from image acquisition devices 26 and transmit the image data to analysis computer 28.

Image acquisition devices 26 may be conventional imaging devices that are capable of reading a sequential portion of the moving web 20 and providing output in the form of a digital data stream. As shown in FIG. 2, imaging devices 26 may be cameras that directly provide a digital data stream or an analog camera with an additional analog to digital converter. Other sensors, such as, for example, laser scanners, may be utilized as the imaging acquisition device. A sequential portion of the web indicates that the data is acquired by a succession of single lines. Single lines comprise an area of the continuously moving web that maps to a single row of sensor elements or pixels. Examples of devices suitable for acquiring the image include linescan cameras such as Piranha Models from Dalsa (Waterloo, Ontario, Canada), or Model Aviiva SC2 CL from Atmel (San Jose, Calif.). Additional examples include laser scanners from Surface Inspection Systems GmbH (Munich, Germany) in conjunction with an analog to digital converter.

The image data may be optionally acquired through the utilization of optic assemblies that assist in the procurement of the image. The assemblies may be either part of a camera, or may be separate from the camera. Optic assemblies utilize reflected light, transmitted light, or transflected light during the imaging process. Reflected light, for example, is often suitable for the detection of defects caused by web surface deformations, such as surface scratches.

In some embodiments, fiducial mark controller 30 controls fiducial mark reader 29 to collect roll and position information from web 20. For example, fiducial mark controller 30 may include one or more photo-optic sensors for reading bar codes or other indicia from web 20. In addition, fiducial mark controller 30 may receive position signals from one or more high-precision encoders engaged with web 20 and/or rollers 22, 24. Based on the position signals, fiducial mark controller 30 determines position information for each detected fiducial mark. Fiducial mark controller 30 communicates the roll and position information to analysis computer 28 for association with detected anomalies.

Analysis computer 28 processes streams of image data from acquisition computers 27. In accordance with the techniques described herein, a feature extraction module 43 executes on analysis computer 28 and dynamically determines which image features to compute on a per-image basis in real-time during manufacture of web material 20. That is, for each sample image acquired during manufacture, feature extraction module 43 builds a "best feature set" in real-time by using the results from successively larger feature sets to trigger additional feature computations until severity levels can be computed for each type of potential non-uniformity. In one example embodiment, computerized non-uniformity charting module 39 ("charting module 39") processes the extracted features by applying algorithms that utilize continuous ranking model 34 ("model 34") developed based on training data 35 to detect the presence of non-uniformity defects and provide a continuous charting of a severity level of each defect. Further details of an example charting module 39 can be found in U.S. Provisional Patent Application 61/394,655, Ribnick et al., entitled "CONTINUOUS CHARTING OF NON-UNIFORMITY SEVERITY FOR DETECTING VARIABILITY IN WEB-BASED MATERIALS".

Training data 35 typically consists of a large set of representative sample digital images that have been assigned ratings by one or more experts 38. Previously automatically ranked data can be used for training as well. The digital images may, for example, represent samples taken from web 20 or another web previously produced by web process line 21. Training server 36 may provide an operating environment for execution of software that provides a computerized expert rating tool 37 ("rating tool 37") to assist experts 38 in efficiently and consistently assigning ratings (i.e., labels) to the large collection of digital images representing the samples. Further details of an example expert rating tool 37 can be found in U.S. Provisional Patent Application 61/394,428, Ribnick et al., entitled "COMPUTER-AIDED ASSIGNMENT OF RATINGS TO DIGITAL SAMPLES OF A MANUFACTURED WEB PRODUCT".

Once training data 35 has been established, training module 41 processes the training data to generate continuous ranking model 34 for subsequent use by charting module 39 for real-time analysis of image data received from acquisition computers 27 for web material 20. In this way, new images of regions of web material 20 can be classified in accordance with continuous ranking model 34. Example defects that may be detected include non-uniformities such as mottle, chatter, banding, and streaks, as well as point defects including spots, scratches, and oil drips.

Analysis computer 28 may stores the anomaly information for web 20, including roll identifying information for the web 20 and possibly position information for each anomaly, within database 32. For example, analysis computer 28 may utilize position data produced by fiducial mark controller 30 to determine the spatial position or image region of each anomaly within the coordinate system of the process line. That is, based on the position data from fiducial mark controller 30, analysis computer 28 determines the x, y, and possibly z position or range for each anomaly within the coordinate system used by the current process line. For example, a coordinate system may be defined such that the x dimension represents a distance across web 20, a y dimension represents a distance along a length of the web, an the z dimension represents a height of the web, which may be based on the number of coatings, materials or other layers previously applied to the web. Moreover, an origin for the x, y, z coordinate system may be defined at a physical location within the process line, and is typically associated with an initial feed placement of the web 20. Database 32 may be implemented in any of a number of different forms including a data storage file or one or more database management systems (DBMS) executing on one or more database servers. The database management systems may be, for example, a relational (RDBMS), hierarchical (HDBMS), multidimensional (MDBMS), object oriented (ODBMS or OODBMS) or object relational (ORDBMS) database management system. As one example, database 32 is implemented as a relational database provided by SQL Server™ from Microsoft Corporation.

Once the process has ended, analysis computer 28 may transmit the data collected in database 32 to conversion control system 4 via network 9. For example, analysis computer 28 may communicate the roll information as well as the anomaly information and respective sub-images for each anomaly to conversion control system 4 for subsequent, offline, detailed analysis in accordance with continuous ranking model 34. For example, the information may be communicated by way of database synchronization between database 32 and conversion control system 4. In some embodiments, conversion control system 4 may determine those products of products 12 for which each anomaly may cause a defect, rather than analysis computer 28. Once data for the finished web roll 10 has been collected in database 32, the data may be communicated to converting sites 8 and/or used to mark anomalies on the web roll, either directly on the surface of the web with a removable or washable mark, or on a cover sheet that may be applied to the web before or during marking of anomalies on the web.

The components of analysis computer 28 and training server 36 may be implemented, at least in part, as software instructions executed by one or more processors of analysis computer 28, including one or more hardware microprocessors, digital signal processors (DSPs), application specific integrated circuits (ASICs), field programmable gate arrays (FPGAs), or any other equivalent integrated or discrete logic circuitry, as well as any combinations of such components. The software instructions may be stored within in a non-transitory computer readable medium, such as random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer-readable storage media. Although shown for purposes of example as positioned within manufacturing plant 6A, analysis computer 28 as well as training server 36 may be located external to the manufacturing plant, e.g., at a central location or at a converting site. For example, analysis computer 28 and training server 36 may operate within conversion control system 4. In another example, the described components execute on a single computing platform and may be integrated into the same software system.

Figure 3:
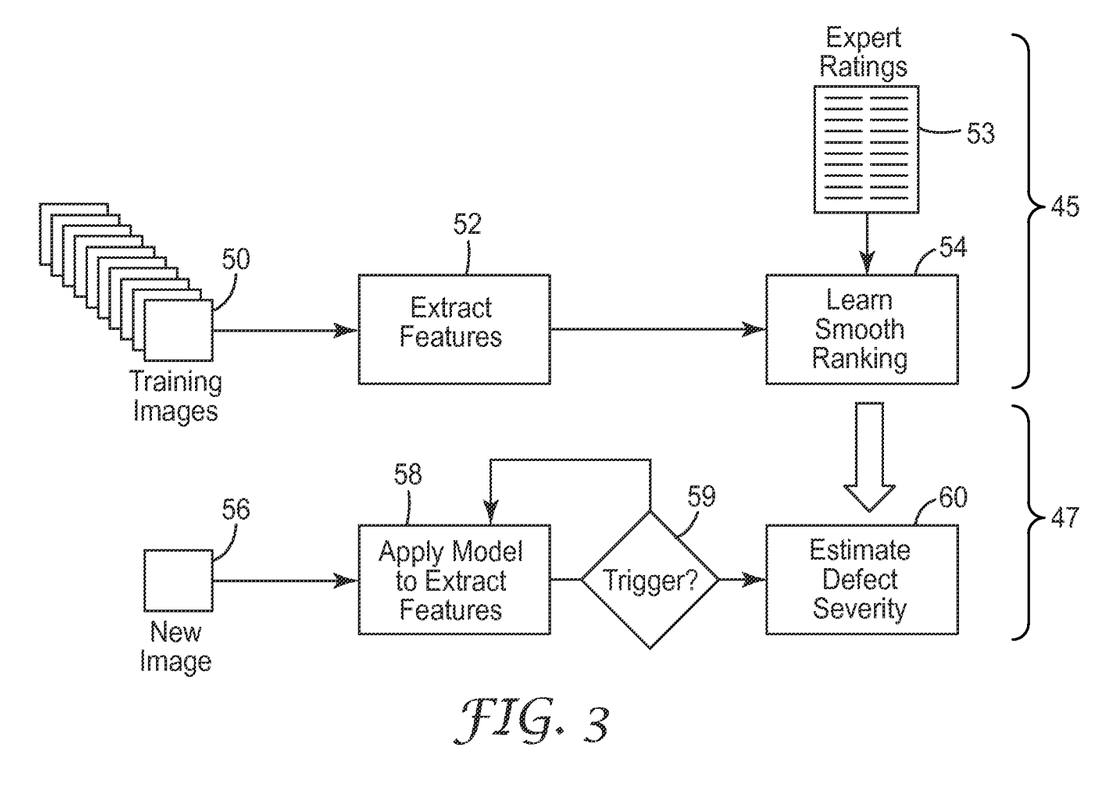
FIG. 3 is a flowchart illustrating an example operation of the systems described herein.

FIG. 3 is a flowchart that provides an overview of the inspection system of FIG. 2. In this example, the process comprises two general phases of processing: training phase 45 and online estimation phase 47. For purposes of example, the inspection system is described with respect producing a measurement of non-uniformity severity of a given sample on a continuous scale or more accurately sampled scale, such as 1.63 on a scale from 0 to 10. The techniques are not limited in the regard and may be applied to other forms of labeling or rating severity of non-uniformity defects within web material.

Initially, training module 41 receives training data 35 as input, typically in the form of a set of images, for which severity rankings are already known on a possibly coarsely discretized scale (50). That is, training data 35 may be digital images representing samples taken from web 20, and computerized expert rating tool 37 ("rating tool 37") may have assigned discrete ratings 53 to each of the digital images in the manner described by U.S. Provisional Patent Application 61/394,428.

Next, a feature extraction software module of training module 41 processes each of the images to extract features (52). Feature extraction provides a numerical descriptor of each of the images as a compact numerical representation of the relevant information inherent in each image. As feature extraction during the training phase occurs offline, the feature extraction software module may perform the complete set of feature extraction computations for each of the training images. Features can be extracted in any way that preserves useful information about the relationships between images in the training set, and at the same time eliminates un-informative image characteristics. Examples of common feature extraction techniques include convolving the image with a set of filters and computing statistics of the filtered images, or extracting features based on color or intensity histograms. Sometimes the pixel values can be used as features, although in this case there is no compactness in the descriptor, since the entire image must typically be stored. In general, the resulting features are treated as compact descriptions of the relevant information in the corresponding images.

The techniques described herein are not limited to use with any particular feature extraction methodology, and may readily be applied to applications in which other types of features are more appropriate. In general, the features extracted from the images are descriptive in that they contain discriminating information about the images with respect to a particular type of non-uniformity. As such, once features have been extracted, the feature vector corresponding to each image represents most of the relevant information contained in that image.

One exemplary feature extraction algorithm, particularly as it relates to texture, is to compute a small covariance matrix of pixel features across the image. Once this small covariance matrix (e.g., 5×5) is extracted, pair-wise comparisons between images can be made efficiently based only on these matrices, instead of dealing with the images directly. For example, a grayscale image is defined as a two-dimensional array, indexed by pixel coordinates x and y, as I(x, y). At each pixel location (x, y), a feature vector is extracted based on the intensity values of the pixel and their first and second derivatives at that pixel:

$$f(x, y) = \left( I(x, y) \quad \frac{\partial I(x, y)}{\partial x} \quad \frac{\partial I(x, y)}{\partial y} \quad \frac{\partial^2 I(x, y)}{\partial x^2} \quad \frac{\partial^2 I(x, y)}{\partial y^2} \right)^T. \quad (1)$$

Image derivatives (gradients) can be approximated simply by computing forward or central differences between intensity values at each pixel. Other features, including higher derivatives or results from filtered image, can be incorporated in the vector in (eq. 1). Similarly, not all derivatives need to be included, e.g., if a derivative in a given direction provides no information for the particular defect, it can be removed from (eq. 1). Finally, the covariance matrix of these pixel features is computed across the entire image:

$$C_I = \frac{1}{N-1} \sum_{(x,y) \in I} (f(x, y) - \mu)(f(x, y) - \mu)^T, \quad (2)$$

where N is the number of pixels in the image, and:

$$\mu = \frac{1}{N} \sum_{(x,y) \in I} f(x, y) \quad (3)$$

is the mean of the pixel features. In subsequent processing steps, it may be useful to compute pair-wise distances between images. In the case of these covariance matrix descriptors, pair-wise distances are computed as:

$$d_C(I_1, I_2) = \sqrt{\sum_{i=1}^{5} \ln^2 \lambda_i (C_{I_1}, C_{I_2})}, \quad (4)$$

where $\lambda_i(C_{I_1}; C_{I_2})$ is the ith generalized eigenvalue of the two covariance matrices. Further details can be found in O. Tuzel, F. Porikli, and P. Meer. "Region Covariance: A Fast Descriptor for Detection and Classification", Proceedings of the European Conference on Computer Vision, 2006.

After extracting features for each of the training images, training module 41 process the feature vectors to learn a continuous ranking of the training images and produce continuous ranking model 34 based on the severity of their non-uniformities (54). During training phase 45, training module 41 learns a continuous ranking of the training images based on the severity of their non-uniformities. Initially, all that is known about each training image is the expert rating, denoting if the corresponding sample is "good" or "bad," or a "1," "3," or "5" with respect to a particular type of non-uniformity. These expert ratings provide an often coarse ordering of the training images, i.e., the training images can be ranked into 2 or 3 discrete categories, or more categories if the operator is able to provide such information. Training model 41 uses this coarse ordering as input and learns a continuous ranking in which the training images are ranked from best to worst along a continuous scale with respect to a particular non-uniformity. Although a good ranking should heed the expert ratings as much as possible, for example assigning "good" images lower severity ranking than those labeled "bad," in some instances training module 41 is not completely prevented from violating the coarse ranking implied by the discrete labels, since it is possible, and indeed common, that there are mistakes in the expert ratings due to the subjectivity of manual labeling of the training data.

During the online estimation phase 47, charting module 39 applies the learned continuous ranking model 34 in real-time on the production line. As a sample image of the web being produced is captured (56), feature extraction module 43 extracts features from the image (58). As described in further detail below, feature extraction module 43 dynamically determines which image features to compute on a per-image basis in real-time during manufacture of web material 20. For each sample image acquired during manufacture, feature extraction module 43 build a "best feature set" in real-time by using the results from successively larger feature sets to trigger additional feature computations. Feature extraction module 43 may store a model (e.g., a Markov model) that defines a chain of dynamic triggers for selecting in real-time which features to extract from the sample image. Feature extraction module 43 applies the model to repeatedly dynamically trigger selection of additional sets of features to extract from the sample image until the extracted features are sufficient to compute a severity level of a non-uniformity defect for the web material (59, 60). As such, the number of features extracted for any given sample image, and the order in which the features are extracted, is dynamically determined in real-time by feature extraction module 43. The computer inspection system may compute the severity level by assigning a severity rating label such as "good" or "bad" or by producing a severity value such as "1.63" on a scale of 1 to 10. The computed severity for the non-uniformity defect may then be output to a user. For example, once the extracted features are sufficient for a severity rating to be assigned based on continuous ranking model 34, the severity rating may be output to the user.

Figure 4:
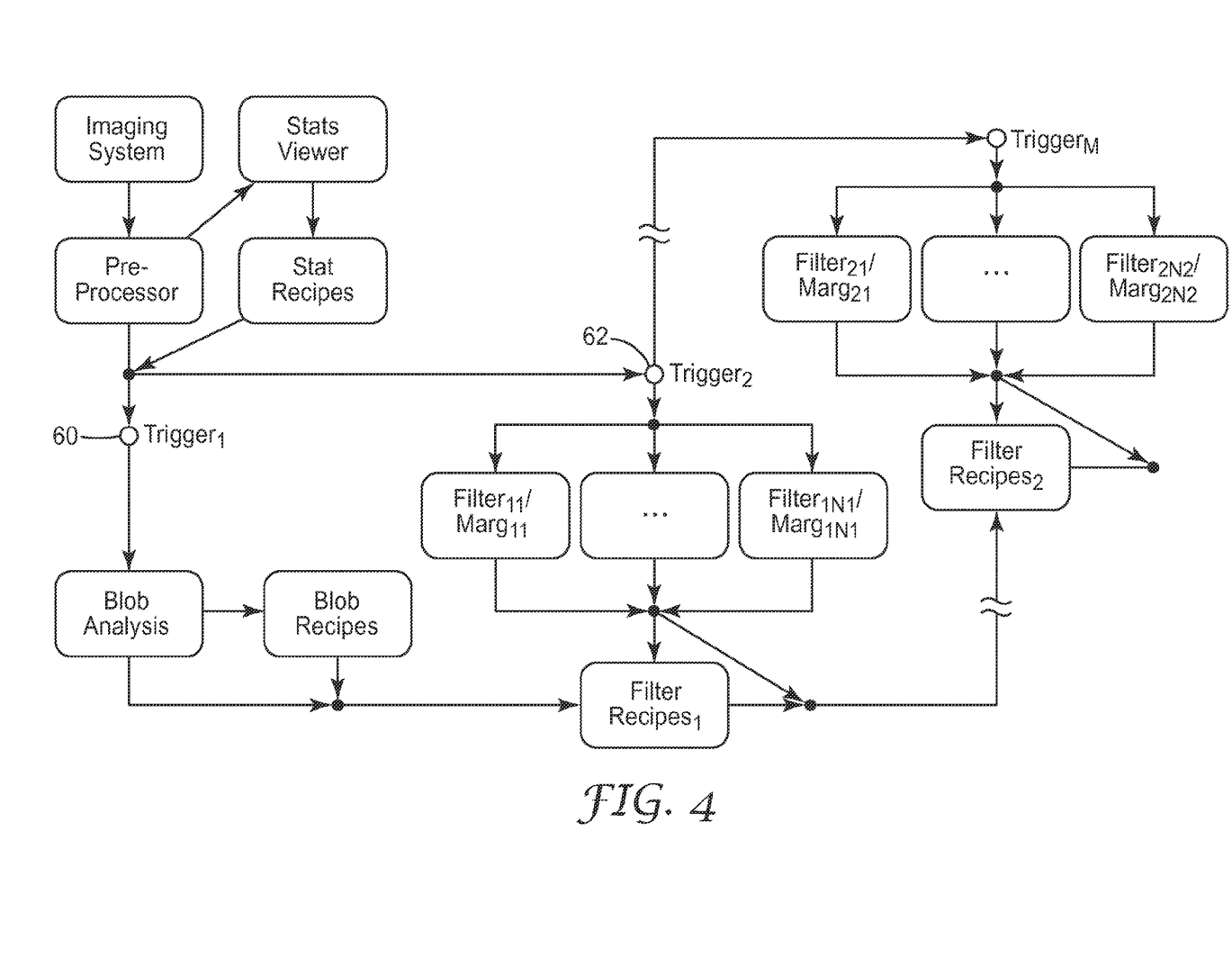
FIG. 4 is a flow diagram showing an example a dynamic system architecture in which a feature extraction module builds a "best feature set" in real-time by using the results from successively larger feature sets to trigger additional feature computations.

FIG. 4 is a flow diagram showing an example a dynamic system architecture in which feature extraction module 43 builds a "best feature set" in real-time by using the results from successively larger feature sets to trigger additional feature computations. After capturing a new image of the web material, analysis computer 28 may perform some pre-processing, such as edge trimming, flattening, or the like, and compute some certain statistics for logging or output display presentation.

Next, feature extraction module 43 reaches a first trigger point 60 where the decision is made whether to trigger additional processing by analyzing the features computed for the new image up to that point in the flow. For example, feature extraction module 43 may apply a base feature set that has been identified by the operator as simpler and faster processing in comparison to the other feature extraction computations. At trigger point 60, feature extraction module 43 may apply some morphological (blob) analysis using so called blob recipes to detect point defects using the base feature set. In parallel, feature extraction module 43 determines whether the base feature set provides sufficient evidence to assess non-uniformity variation within the new image within a level of confidence. For example, the decision regarding whether or not to trigger more features in order to help classify the current image can be made according to a simple heuristic. For example, one may set a simple decision rule such that, if an expected reduction in cost of misclassifying the image with respect to the non-uniformity defect from adding the dynamically determined next-best set of features is above some threshold, then feature extraction module triggers extraction of the additional features. The expected reduction in cost, i.e., the required level of confidence, can be determined using the learned Markov model, as further described below. If not, feature extraction module 43 proceeds to trigger point 62 and triggers successively more complex processing. That is, at second trigger point 62, feature extraction module 43 performs a second set of feature extraction computations, e.g., image filtering/marginalization, in order to extract additional features. This second set of feature extraction computation may be more complex and computationally intensive than the base feature set initially performed. Feature extraction module 43 again attempts to identify and degree and type of non-uniformity using image recipes, also referred to as classifiers, which are mathematical models whose inputs are some or all of the features extracted for the new image up to this point in the flow.

The processes repeats as a chain of trigger points 60M, where at each trigger point the decision is made whether additional, more complex, image processing computations are necessary in order to determine the degree at which any type of non-uniformity exists within the image. This determination at each trigger point is made based on the features computed for the new image up to that point in the flow.

In some situations, a sample image captured in real-time from the web material may contain multiple patterns. In accordance with the process set forth in FIG. 4, feature extraction module 43 operates such that the features that are likely to enable the most accurate classification of any non-uniformity are triggered. This process may be performed for every individual sample imaged by the computerized inspection system. Alternatively, feature extraction module 43 may operate under a polling scheme, in which the necessity to trigger or retract process components is checked after every X samples, where X is a configurable parameter.

In one example, feature extraction module 43 is configured to operate in accordance with a controlled Markov model for dynamic triggering. In this embodiment, feature extraction module 43 includes configuration data that defines a state vector x(t) which serves as a sufficient summary of information at any triggering step t relevant to future triggering events. For completeness, a triggering event any point in the process for analyzing a single image sample where feature extraction module 43 has an opportunity to select additional features to compute.

In one example, the state vector is defined through a family of classifiers $\{\phi_i(t)\}_{i=1}^{N}$, where at triggering step t, $\phi_i(t)$ only depends on the features triggered at step t and classifier family at the previous step $\{\phi_i(t-1)\}_{i=1}^{N}$. An example of how such a sequence of classifier families may be constructed using the ROC-optimal classifier enhancement algorithm is described in PCT International Application Publication No. WO/2010/059679. In this example, the binary classifier consists of a set of decision rules (i.e., thresholds on possibly multiple variables) that are learned from labeled training data. However, in general any discrete classification algorithm could be used. Other examples included Support Vector Machines (SVM), Logistic Regression, or Decision Trees.

With respect to defining the state vector of feature extraction module 43, the $i^{th}$ element of the state vector at step t is taken as the classification assigned by $\phi_i(t)$, i.e. $x_i(t)=\phi_i(t)$. One example is binary classification, so that $x(t) \in \{0, 1\}^N$, however, the method discussed herein can be extended to the multinomial case.

The configuration data of feature extraction module 43 includes a control variable that determines the action at a given trigger event, i.e., the additional set of one or more features not already computed that are designated to be computed next. To simplify the discussion, it is assumed a single feature f is to be selected at each trigger event. However, the algorithm is similar if f is taken to represent a plurality of features instead. Since the classifiers determine the state vector through judgments on the current sample image, and they only depend on f and the family of classifiers at the previous step, feature extraction module 43 computes a prediction of a future state vector on the basis of the current state vector using the conditional distribution $P_f(x(t+1)|x(t))$ parameterized by the control f to be optimally chosen. That is, $P_f$ is referred to as the transition function of the Markov chain. Feature extraction module 43 estimates the transition function in order to implement a control strategy. Given a training set of sample images and associated sequence of classifier families, feature extraction module 43 may be configured to use a simple histogram estimate $\hat{P}_f$, where $\hat{P}_f(x(t+1)|x(t))$ is the number of training samples for which the state at step t is x(t) and the state at step t+1 is x(t+1) when feature f is selected. To avoid problems associated with high dimensions, including noisy $\hat{P}_f$ and sparse sampling of the space, N may be selected to be small. Alternatively, feature extraction module 43 may be configured to utilize parameterization or kernel smoothing of $\hat{P}_f$.

With these components in place, feature extraction module 43 dynamically selects fat any triggering event utilizing the transition function estimate to choose an f that minimizes some expected loss. For example, assume a value $c_{a|b}$ is assigned as a cost of misclassifying an a as a b (with a,b∈{0, 1}), then if $x_i(t)=1$, the expected loss of using classifier i is made under the assumption that it is a mistake (i.e. the true class is 0). This gives an expected loss $c_{1|0} p_t(0) FA_f^i$ where $p_t(0)$ is the prior probability any given sample is truly 0, and $FA_f^i$ is the false alarm rate ($p_t(0|1)$) of classifier i (explicitly indexed by current control f to emphasize the dependence). Similarly, when $x_i(t)=0$, the expected loss of using classifier i is $c_{0|1}p_t(1)(1\ 31\ CD_f^i)$ where $CD_f^i$ is the correct detection rate $p_t(1|1)$ of classifier i. The loss function can be expressed as:

$$C_t(x,f)=\min\{c_{1|0}p_t(0)\min_{rx^j=1}FA^i_{f},cC_{1|0}p_t(1)\min_{rx_f=0}(1-CD^i_f)\}$$

As one example, feature extraction module 43 utilizes a control strategy that minimizes the total expected cost over all trigger events $\Sigma_t c_t(x,f)$. This problem can be solved exactly via dynamic programming if the sizes of the state and control spaces are not too large. Alternatively a greedy heuristic may applied at each step, selecting $f^*_t=\min_f c_t(x,f)$, to find a reasonable sub-optimal solution. In one embodiment, all possible trigger event trajectories are computed offline and feature extraction module 43 is programmed to use a look-up table online. In this way, it is possible to reduce the number of features computed for each sample image using a controlled Markov chain model for triggering the most discriminative features for the current sample. Thus, the features selected in response to any triggering event may be dynamically determined based on the currently extracted features and computed transition function.

The techniques described above can easily be extended to the multi-classifier case using, for example, a simple sum of single classifier loss functions. Also, $c_{a|b}$, can be scaled differently for different defect categories to capture relative importance or include an additive factor corresponding to feature dependent computation time. Further, the techniques above have been explained with respect to an example cost function. Other possibilities exist. For example, one might also consider a cost function that penalizes entropy of the class posterior distribution.

EXAMPLES

A simulation study was conducted using film images collected from a process development line. The complete sample set contains 8767 images that exhibited a variety of non-uniformities. Broadly, the non-uniformities can be grouped into seven categories. In addition to the chatter and (large) mottle categories, there are small mottle, bar marks/banding, splotches/watermarks, streaks, and diagonal variation defects. A sequence of classifier families were designed for each separate category. That is, seven different Boolean classifier family sequences (one for each non-uniformity category) were designed that determine presence/absence of a non-uniformity by thresholding selected features from a set 26 statistical and spectral features extracted using histogram and Gabor filter processing. The classifiers designed in accordance with the techniques described in PCT Application WO/2010/059679 and were trained on the complete sample set.

Each classifier family sequence was designed to contain successively more complex classifiers (i.e. using more features), where each successive classifier in a give family sequence tended to assign the non-uniformity to its targeted category with higher accuracy. A trigger event was defined as the advancement of a single selected classifier family to the next most complex set of classifiers in its sequence. This corresponds directly to computing an additional set of features for the current sample at each trigger event, since it is additional features that enable the advancement in a classifier family sequence.

Figure 5:
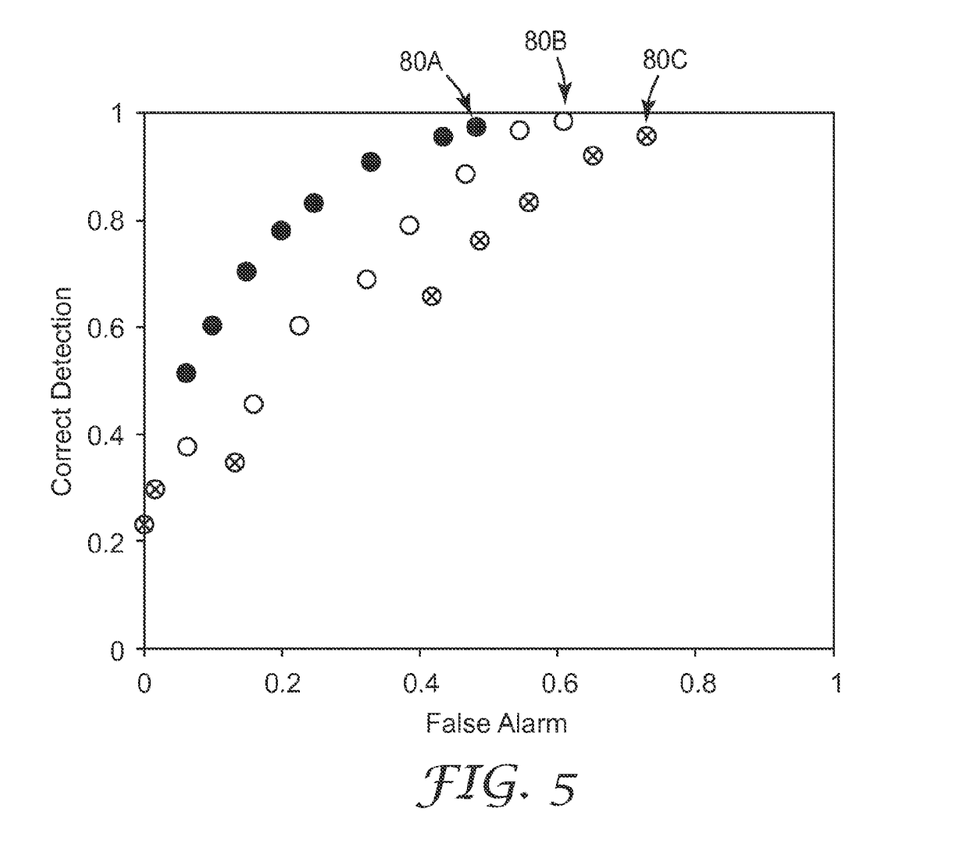
FIG. 5 shows the performance of a three-step sequence in ROC-space.

FIG. 5 shows the performance of a three-step sequence in ROC-space. As shown, each family 80A, 80B and 80C consisted of eight classifiers. The fact that the sequence is approaching the upper left corner of the ROC plot indicates improving performance at each step (red, then green, then blue).

Figure 6:
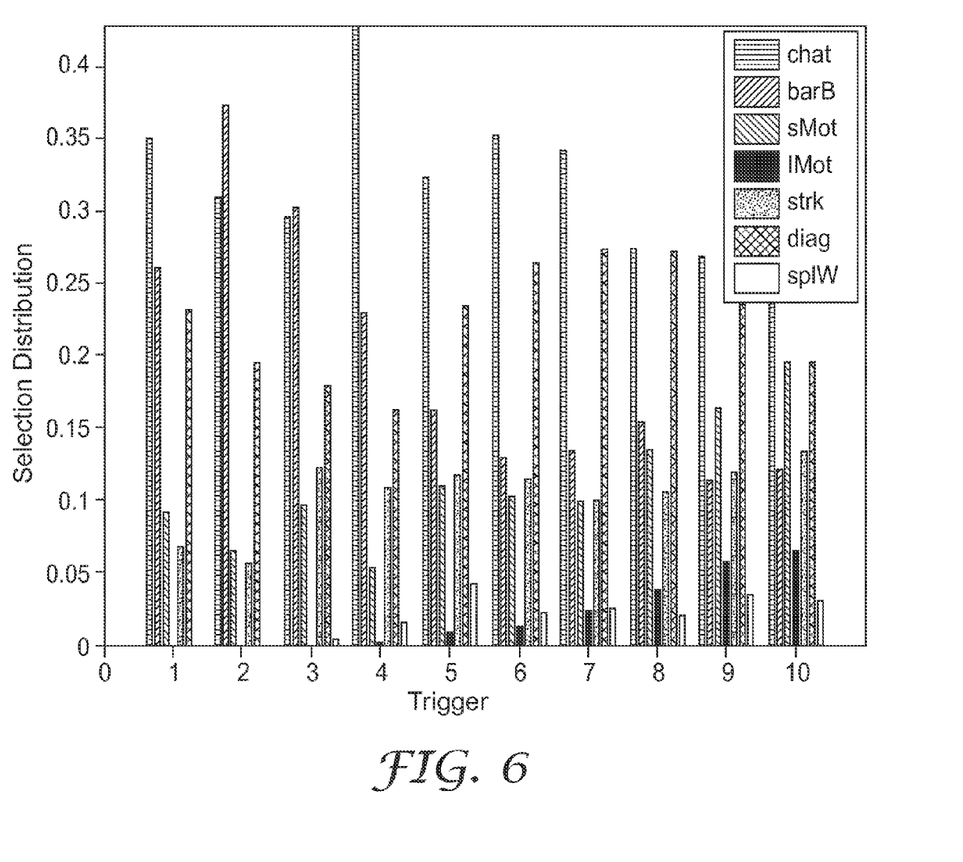
FIG. 6 is a histogram that illustrates the difference between baseline random and greedy optimal methods.

A single simulation trial involved choosing 50 random image samples from the set of 8767 and analyzing each over ten trigger events, where each event was an advancement of a single defect category's classifier family. We computed the "best" ten triggers for each sample using the method described here with a "one step ahead" greedy optimization and all misclassification errors assigned unit cost. This was compared to a random trigger selection for each sample, where the ten trigger events were selected at random from the set of all possible triggers. To assess average performance, 1000 simulation trials were performed. FIG. 6 is a histogram that illustrates the difference between the baseline random (A) and greedy optimal (B). These histograms are aggregated over the 1000 trials and 50 image samples at each trial.

Figure 7:
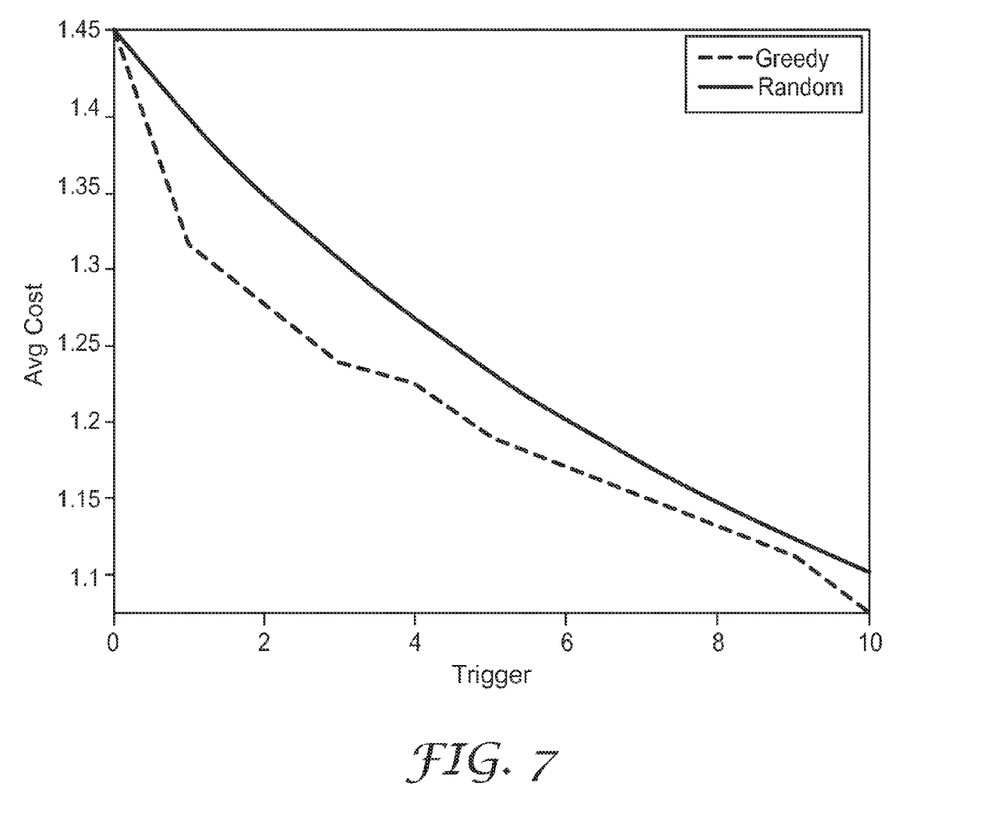
FIGS. 7 and 8 are plots showing performance results based on the simulation study.
Figure 8:
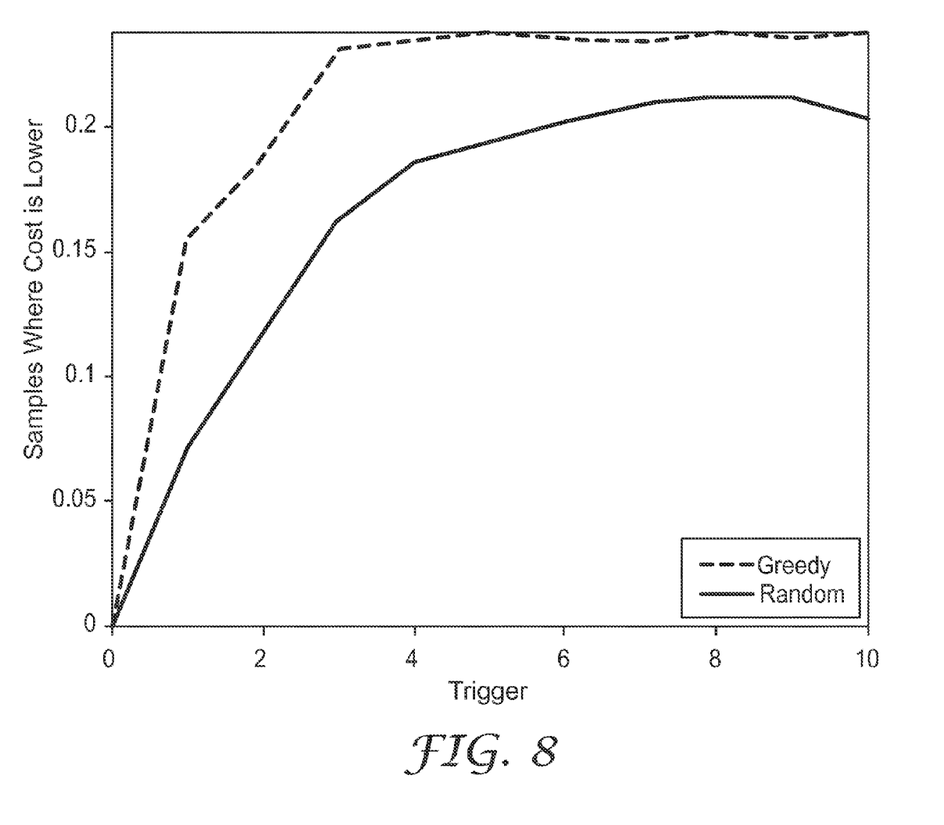

FIGS. 7 and 8 are plots showing performance results based on the simulation study. FIG. 7 illustrates the average miss-classification cost across trials/images. As described above, all miss-classifications were assigned a unit cost. As shown, the greedy optimal controlled trigger has lower average cost across all events than a random trigger with the most substantial difference observed after the first couple of triggers. FIG. 8 is a comparative plot that shows the average (across trials) fraction of the 50 samples in which a particular triggering strategy yielded a lower cost. As shown, the greedy trigger gave better performance on average for a larger proportion of the 50 samples.

The controlled Markov chain model for feature triggering is demonstrated to give a clear improvement. Further improvement may be gained by using more sophisticated control optimization since the greedy algorithm may be considered a simple yet efficient scheme. Also, the set of features considered in the study is relatively small (26 features). The techniques may be even more advantageous when it is necessary to choose from a larger feature set. In such cases, dynamically discovering the best features to compute may have even more advantage in a live production line. There is minimal online computation associated with this technique since, in one embodiment, it can be implemented through a table lookup and the expensive construction of the lookup table can be done offline.

An alternative case of triggering is when images are compared to recent past frames to control for continuation of the current quality, and a change is detected, triggering more detailed analysis. For example, if the current web is in the stage of "good web," often simple features such as variance can be used to detect the appearance of a new non-uniformity. This detection triggers more detailed analysis, which then calls for the computation of additional features.

In addition, recent past sample images obtained from a material in an online product line can be charted following the procedure described in the U.S. Provisional Patent Application 61/394,655, Ribnick et al., entitled "CONTINUOUS CHARTING OF NON-UNIFORMITY SEVERITY FOR DETECTING VARIABILITY IN WEB-BASED MATERIALS". Following the procedure described therein, a new sample image (frame) can be charted. This can be done with previously labeled training data, a set that can be augmented with the recently charted frames. Once a significant change in charting value is discovered, triggering occurs, calling for an augmented set of features to detect the class and severity of any non-uniformity within the new frame.

Various embodiments of the invention have been described. These and other embodiments are within the scope of the following claims.

The invention claimed is:

1. A method for inspecting web material in real-time and computing a severity of a non-uniformity defect as the web material is manufactured, the method comprising:
receiving, with an online computerized inspection system, an image captured from a web material being manufactured;
processing the image with the inspection system to extract a first set of features;
processing the first set of features with the inspection system with a model to dynamically select a second set of features to extract from the image in accordance with the model;
determining, in accordance with the model, an expected reduction in cost of misclassifying the image with respect to the non-uniformity defect if the second set of features are extracted from the image;
when the expected reduction in cost exceeds a threshold, processing the image with the inspection system to extract the second set of features; and
computing the severity level for the non-uniformity defect for the web material with the inspection system using the first set of features and the second set of features extracted from the image.

2. The method of claim 1, wherein the model comprises a Markov model that defines a chain of one or more dynamic triggers for controlling the selection of the second set of features to extract and any additional sets of features to extract from the image.

3. The method of claim 2, further comprising:
defining a current state vector that specifies a family of classifiers;
computing a prediction of a future state vector on the basis of the current state vector using a conditional distribution parameterized by at least one of the first set of features, wherein the conditional distribution represents a transition function for the dynamic trigger of the Markov model; and
dynamically selecting the second set of features from an overall set of features based on the computed transition function.

4. The method of claim 3, wherein dynamically selecting the second set of features comprises selecting the second set of features to minimize a total expected cost associated with selecting any of the overall set of features.

5. The method of claim 1, further comprising:
processing the second set of features with the inspection system with the model to dynamically select a third set of features to extract from the image in accordance with the model;
determining, in accordance with the model, a second expected reduction in cost of misclassifying the image with respect to the non-uniformity defect if the third set of features are extracted from the image;
when the second expected reduction in cost exceeds the threshold, processing the image with the inspection system to extract the third set of features; and
computing the severity level for the non-uniformity defect for the web material with the inspection system using the first set of features, the second set of features, and the third set of features extracted from the image.

6. The method of claim 1, wherein computing the severity level comprises applying one or more classifiers to determine whether a rating label for the non-uniformity defect can be determined.

7. The method of claim 1, further comprising:
prior to receiving the image with the online computerized inspection system, executing software on a computer to extract features from each of a plurality of training images by computing a numerical descriptor for each of the training images from pixel values of the respective training image, wherein each of the images has been assigned one of a set of discrete rating labels for a non-uniform defect present within the training images; and
processing the numerical descriptors of the training images with the rating software to compute a continuous ranking of the training images based on the discrete rating labels assigned to the training images,
wherein, processing computing the severity level with the online computerized inspection system comprises computing the severity level for the non-uniformity defect in accordance with the continuous ranking.

8. The method of claim 1, further comprising presenting a user interface to output the severity level to a user.

9. The method of claim 8, wherein presenting a user interface comprises updating a chart to graph the severity level of the non-uniform defect for the web material over time.

10. The method of claim 8, further comprising:
receiving input from the user; and
adjusting a process control parameter for the manufactured web material in response to the input.

11. The method of claim 1, wherein processing the image to extract the first set of features comprises invoking hardware components of a pipelined graphical processing unit (GPU) integrated within the inspection system to process the image and extract the first set of features in parallel.

12. A non-transitory computer-readable medium comprising software instructions to cause a computer processor to:
receive, with an online computerized inspection system, an image captured from a web material being manufactured;
process the image with the inspection system to extract a first set of features;
process the first set of features with the inspection system to determine whether a severity level of a non-uniform defect for the web material can be computed;
upon determining that the severity level cannot be computed from the first set of features, apply a model to dynamically select a second set of features to extract;
process the first set of features with the inspection system with a model to dynamically select a second set of features to extract from the image in accordance with the model;
determine, in accordance with the model, an expected reduction in cost of misclassifying the image with respect to the non-uniformity defect if the second set of features are extracted from the image;
when the expected reduction in cost exceeds a threshold, process the image with the inspection system to extract the second set of features; and
compute the severity level for the non-uniformity defect for the web material with the inspection system using the first set of features and the second set of features extracted from the image.

* * * * *

UNITED STATES PATENT AND TRADEMARK OFFICE
CERTIFICATE OF CORRECTION

PATENT NO. : 9,031,312 B2  
APPLICATION NO. : 13/882781  
DATED : May 12, 2015  
INVENTOR(S) : Ribnick et al.

Page 1 of 1

It is certified that error appears in the above-identified patent and that said Letters Patent is hereby corrected as shown below:

In the Specification

Column 7  
Line 45, Delete "an" and insert -- and --, therefor.

Column 10  
Line 6, Delete "λi(C11; C12)" and insert -- λi(CI1; CI2) --, therefor.

Column 13  
Line 1, Delete "(131 CDif)" and insert -- (CDif) --, therefor.  
Line 4-5, Delete

"$C_i(x,f)=\min\{c_{1|0}p_i(0)\min_{i:x_i=1}FA^i_f, cC_{1|0}p_i(1)\min_{i:x_i=0}(1-CD^i_f)\}$"

and insert

-- $C_i(x,f) \equiv \min\{c_{1|0}p_i(0)\min_{i:x_i=1}FA^i_f, C_{1|0}p_i(1)\min_{i:x_i=0}(1-CD^i_f)\}$ --, therefor.  
Line 25, Delete "$c_{a|b}$," and insert -- $c_{a|b}$ --, therefor.  
Line 56, Delete "give" and insert -- given --, therefor.

Signed and Sealed this  
First Day of March, 2016

Michelle K. Lee  
*Director of the United States Patent and Trademark Office*